United States Patent [19]

Corso, Jr.

[11] Patent Number: 5,406,960
[45] Date of Patent: Apr. 18, 1995

[54] GUIDEWIRE WITH INTEGRAL CORE AND MARKER BANDS

[75] Inventor: Philip P. Corso, Jr., Davie, Fla.
[73] Assignee: Cordis Corporation, Miami Lakes, Fla.
[21] Appl. No.: 226,971
[22] Filed: Apr. 13, 1994
[51] Int. Cl.⁶ .................................. A61M 25/00
[52] U.S. Cl. ............................. 128/772; 128/657
[58] Field of Search ............... 128/657, 772; 604/95, 604/164, 170, 171, 280, 281, 282

[56] References Cited

U.S. PATENT DOCUMENTS

| Re. 33,991 | 5/1992 | Samson et al. | 128/772 |
| 3,906,938 | 9/1975 | Fleischhacker | 128/772 |
| 4,763,647 | 8/1988 | Gamble | 128/772 X |
| 4,846,186 | 7/1989 | Box et al. | |
| 4,922,924 | 5/1990 | Gamble et al. | |
| 4,941,743 | 7/1990 | Tenerz et al. | 128/772 X |
| 5,095,915 | 3/1992 | Engelson | 128/772 |
| 5,238,005 | 8/1993 | Imran | 128/772 |
| 5,267,574 | 12/1993 | Viera et al. | |

FOREIGN PATENT DOCUMENTS 377453 7/1990 European Pat. Off. ............ 128/772

*Primary Examiner*—Sam Rimell
*Attorney, Agent, or Firm*—Armstrong, Westerman, Hattori, McLeland & Naughton

[57] ABSTRACT

A guidewire, such as for percutaneous angioplasty, having a radiopaque internal corewire and a spring of radiopaque material at a distal tip portion of the corewire. A plurality of alternating grooves and bands are integrally formed from the corewire in a section adjacent the tip portion of the corewire. A plastic sleeve is attached to the corewire around the integral radiopaque bands.

18 Claims, 2 Drawing Sheets

GUIDEWIRE WITH INTEGRAL CORE AND MARKER BANDS

FIELD OF THE INVENTION

The present invention relates to a novel flexible elongated guidewire used to position a catheter within a patient.

BACKGROUND ART

Percutaneous angioplasty is a therapeutic medical procedure than can increase blood flow through a blood vessel. It can sometimes be used as an alternative to coronary by-pass surgery, for example. An elongated catheter having a deflated balloon at its distal end is guided through a patient's cardiovascular system to the coronary artery of the heart. The balloon is inflated to compress deposits that have accumulated along the inner walls of the coronary artery to widen the artery lumen and increase blood flow.

A known technique for positioning the balloon catheter uses an elongated guidewire that is inserted into the patient and routed through the cardiovascular system as guidewire progress is viewed on an x-ray imaging screen.

Representative prior art patents that disclose flexible, elongated guidewires are U.S. Pat. Nos. 4,545,390 to Leary, 4,538,622 to Samson et al. and 3,906,938 to Fleischhacker. The Leary '390 patent discloses a narrow flexible guidewire having a distal portion that tapers and includes a flexible coiled spring at its distal end. Also representative are U.S. Pat. No. 4,846,186 to Box et al. and U.S. Pat. No. 5,267,574 to Viera et al., both of which are incorporated herein by reference.

One problem with currently available guidewires concerns the visibility of the guidewire. If the guidewire is fully opaque on a viewing screen, it can hinder viewing of post angioplasty angiograms used in studying the results produced by the angioplasty. Guidewires that have only an opaque tip do not adequately depict the arterial path on the viewing monitor.

One prior art guidewire includes an elongated core wire including a flexible reduced diameter distal end and a spring made up of multiple coils of wire wound to form a first, generally uniform diameter spring portion. The spring is constructed of a radiopaque material so that the tip of the guidewire is radiopaque when viewed on a fluoroscope or an x-ray. Most preferably, only a short segment of the guidewire (approximately 3-5 cm) is radiopaque so that the physician's view of the subject just proximal of the guidewire tip is not impeded.

Guidewires have been proposed which, in addition to a fully opaque tip, include an adjacent section of lesser radiopacity. This adjacent section is constructed to achieve a lesser degree of radiopacity by means of alternating radiopaque and non-radiopaque coils, or by means of a plurality of individual radiopaque rings attached to the core of the guidewire.

More particularly, in one prior art guidewire, a plurality of highly radiopaque rings are spaced from each other along a segment of the core wire adjacent to the distal portion of the guidewire having the radiopaque spring. In this way, this adjacent portion of the guidewire is provided with a moderate degree of radiopacity. The rings in this adjacent section can be held in place under a sleeve of non-radiopaque material. The rings aid an attending physician in monitoring the position of the guidewire. A problem with this guidewire is that in manufacturing, it is necessary to provide a step of attaching each of the individual rings to the core. This can be burdensome and costly.

In the prior art there has also been proposed alternating radiopaque and non-radiopaque coils around the segment of the core wire proximal to the distal spring portion of the guidewire. The radiopaque coil can be formed from a highly radiopaque metal, and the non-radiopaque coil can be formed from a flexible non-radiopaque polymer. The distal spring portion of the guidewire is formed solely from a radiopaque material so that the resulting guidewire provides a distal spring having high radiopacity, as well as a proximal section of moderate radiopacity. When constructing such a guidewire, steps must be followed for attaching the alternating radiopaque and non-radiopaque coils to the guidewire core, which can be difficult and detrimental.

DISCLOSURE OF THE INVENTION

The present invention alleviates many of the problems concomitant with the prior art. The present invention provides a guidewire that is simple in construction and easy to manufacture, and enables superior viewing of the operation being performed.

In accordance with the present invention, a guidewire is provided which comprises an elongated corewire having a first section at a distal portion thereof and a second section proximal to said first section. A coiled radiopaque spring surrounds the first section of the corewire and is attached to the corewire. A plurality of radiopaque bands are formed integrally from the corewire in the second section of the corewire.

In accordance with the present invention, a method is provided for making the guidewire. The method comprises extruding or drawing a rod to form a corewire of a predetermined thickness; forming a taper in the corewire by grinding so as to achieve a desired degree of taper in adjacent first and second sections of the corewire; and forming alternating grooves and bands in the second section of the corewire which is proximal to the first section, by grinding a plurality of grooves at predetermined positions along the second section of the corewire such that the bands are formed integrally from the corewire.

A guidewire constructed in accordance with an illustrative embodiment of the present invention includes a first tapered portion and a second tapered portion. In the first tapered portion at the far distal end of the guidewire, a coil is wound therearound. The coil at this first tapered portion is constructed of a radiopaque material so that the tip of the guidewire is radiopaque when viewed on a fluoroscope or an x-ray.

In the second tapered portion proximal to the first (distal) tapered portion, a plurality of spaced marker bands are disposed, formed integrally with the core. The plurality of marker bands are, for example, formed by grinding a plurality of grooves in the core so as to form alternating regions of greater and lesser core diameter, i.e. marker bands and grooves, respectively. The integral marker bands provide a region of moderate radiopacity proximal to the highly opaque tip. The integral marker bands are formed out of the core itself and thus need not be separately attached to the core. Furthermore, the alternating band and groove structure can improve the flexibility of the guidewire and can aid an attending physician in monitoring the position of the guidewire without fully obstructing visualization of arteries in which the guidewire has been inserted.

These and other objects, advantages and features of the invention will become better understood from the following detailed description that describes a preferred embodiment of the invention in conjunction with the accompanying drawings.

DETAILED DESCRIPTION OF THE PREFERRED EMBODIMENTS

Figure 1:
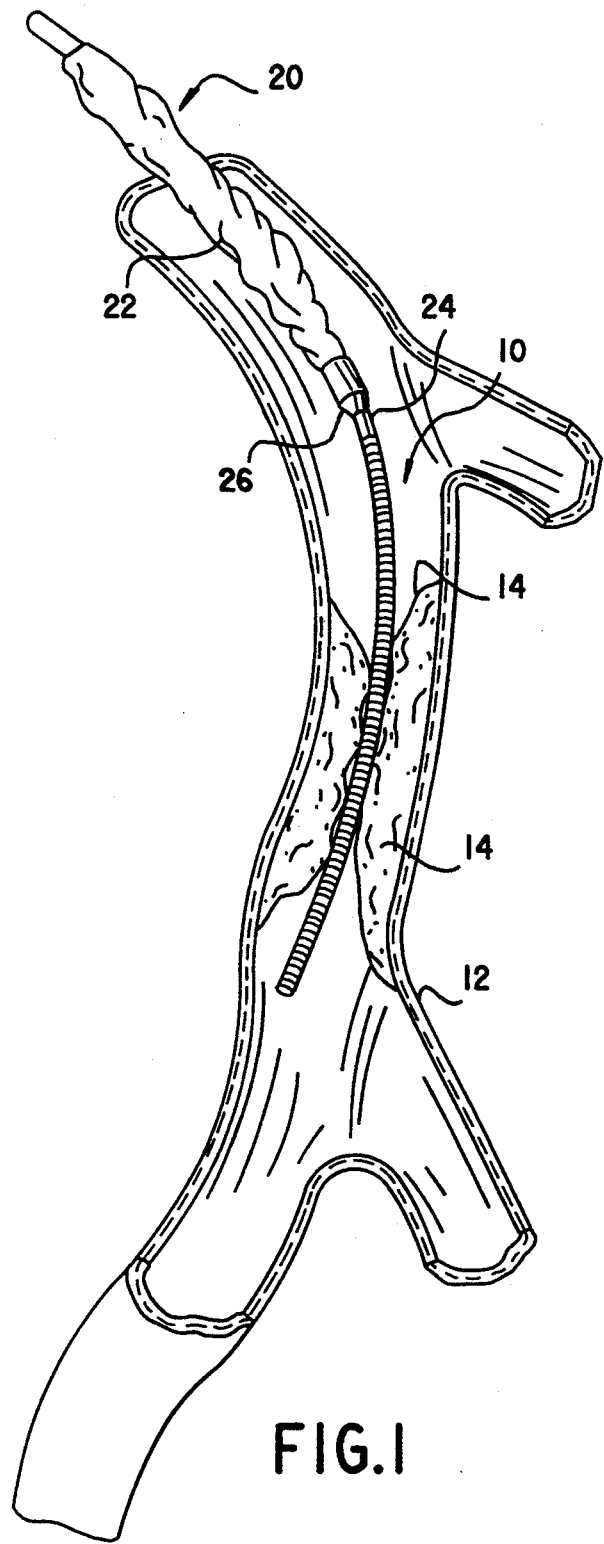
FIG. 1 is a diagrammatic view showing a blood vessel that has been occluded with deposits along an inner wall and showing the positioning of a flexible guidewire within the blood vessel.

Turning now to the drawings, FIG. 1 illustrates a distal portion of a flexible, small diameter guidewire 10 that can be guided through a patient cardiovascular system. A distal end of the guidewire is shown in FIG. 1 within a region in a blood vessel 12 having occlusions 14 which restrict blood flow through the blood vessel 12. The guidewire 10 is long enough to be routed from a patient entry point through the patient to the obstructed blood vessel region. As the guidewire 10 is inserted along the tortuous path to the obstructed blood vessel region, an attending physician conducting the procedure monitors progress of the guidewire 10 on a viewing screen.

The FIG. 1 depiction illustrates use of a guidewire for routing a balloon catheter 20 to the vicinity of the obstructions 14. The balloon catheter 20 includes a passageway or lumen (not shown) that extends from a proximal location outside the patient to a distally located balloon 22. Fluid is routed into the catheter through this lumen to inflate the balloon 22. A distal tip portion 24 of the catheter 20 includes a marker band 26 to aid the attending physician in monitoring balloon catheter progress as it is positioned within the patient. A second, center passageway or lumen in the catheter 20 has a diameter sufficient to accommodate the guidewire 10 so that once the guidewire is properly positioned within the subject, the catheter 20 can be slid over the guidewire.

The distal tip portion of the guidewire 10 is flexible and can be bent to a predetermined configuration to facilitate routing the guidewire 10 along the cardiovascular system to the FIG. 1 region of the blood vessel 12. The pre-bent tip can be re-oriented by the physician. Torques applied to the proximal end of the guidewire are transmitted along the length of the guidewire and re-orient the distal tip to point in a desired direction.

In use, a distal end of the guidewire 10 is routed through a narrow passageway 14a in the obstruction 14 and the balloon catheter 20 slipped over the guidewire until the balloon 22 is located in the region 14 of obstructions within the blood vessel 12. The balloon 22 is then inflated and the balloon's outer surface contacts the obstruction 14. The inner walls of the obstruction 14 are compressed and a wider lumen or passageway created in the blood vessel 12.

Figure 2:
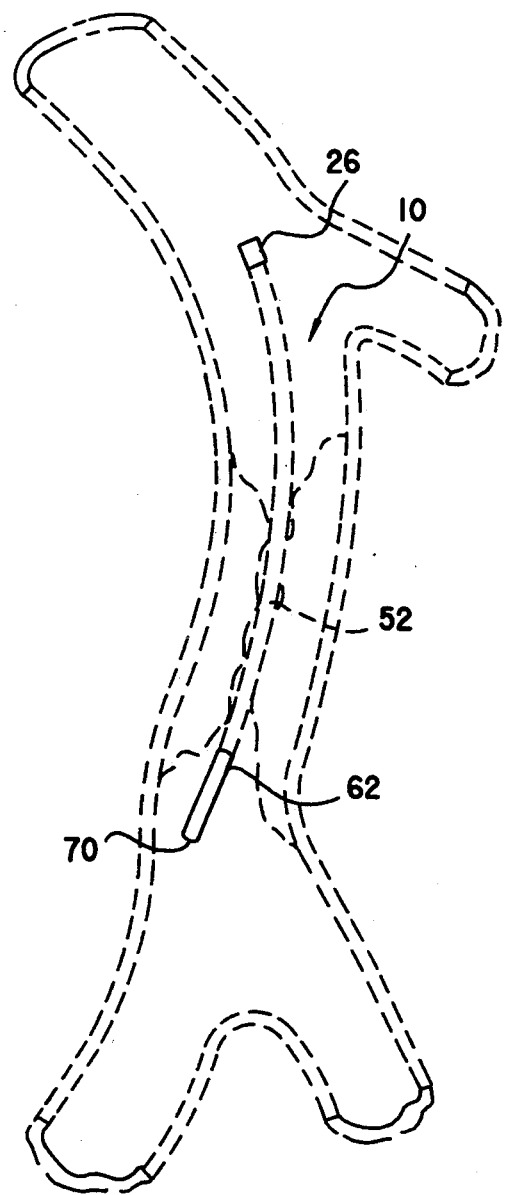
FIG. 2 is a view of a flexible guidewire constructed in accordance with the invention as it appears when viewed on a fluoroscopic examining screen.

FIG. 2 illustrates the image of the guidewire 10 which a physician would see while using the guidewire during angioplasty. As described in detail below, the guidewire 10 is constructed to include a first section 62 and a second section 52 of controlled radiopaqueness that appear when the blood vessel 12 is monitored on a viewing screen. Unlike a fully radiopaque guidewire, the visible section 62 is limited to the distal guidewire tip. Section 52 having bands 38 is visible to aid the physician in adequately tracing the guidewire during angioplasty, but minimizes interference with a post procedure angiogram. The interference is minimized because the radiopacity of the sections 52, 62 can be varied and most preferably the radiopacity of the second section 52 is less than the first section 62.

Figure 3:
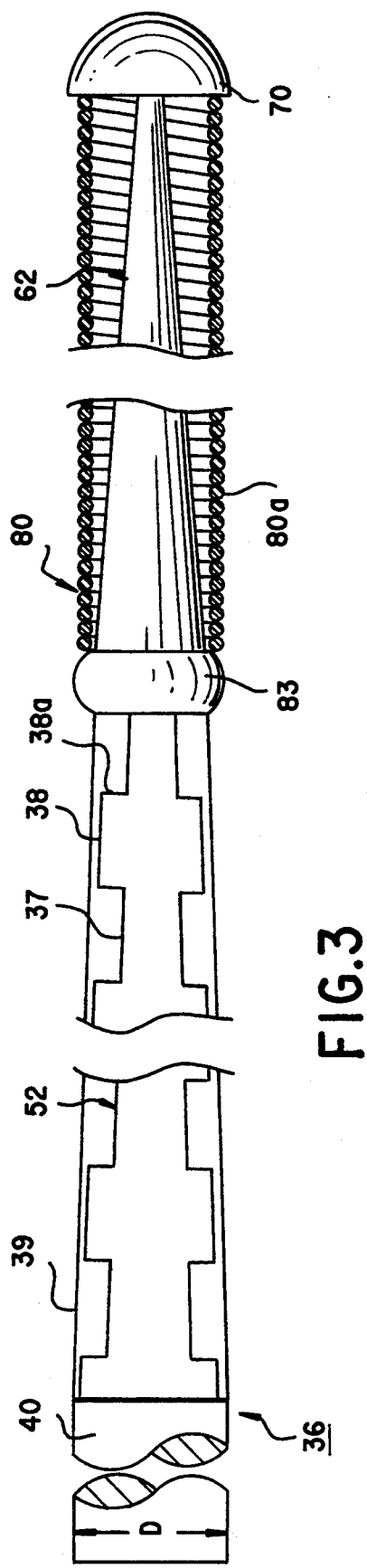
FIG. 3 is an elevational segmented view of a flexible guidewire constructed in accordance with the invention.

Turning now to FIG. 3, the guidewire 10 is seen to include a center metallic core 36 having a proximal uniform diameter portion 40 having a diameter D, extending well over half the length of the guidewire. Through not limited to any diameter, the diameter can be from 0.010–0.038 inch, and preferably 0.010–0.021 inch. To improve the depiction of details of the distal portion of the guidewire 10, this uniform diameter elongated portion 40 has been sectioned and a major portion of its length deleted from FIG. 3. The uniform diameter portion 40 is typically covered with a suitable coating to make its outer surface lubricous.

As also seen in FIG. 3, at the second section 52, core 36 includes grooves 37 and bands 38. Bands 38 are integral extensions of core 36 and are formed from core 36 as will be described hereinbelow. The sidewalls 38a of bands 38 can extend perpendicularly to the axis of the corewire such as illustrated in FIG. 3. Of course, other configurations of the sidewalls 38a of bands 38 are possible, such as sidewalls 38a extending at an angle other than 90 degrees from the corewire axis, extending as a curve rather than as a straight sidewall, etc.

At the first section 62 at the far distal end of the guidewire, the corewire 36 again tapers uniformly and has a length of approximately 1 inch and can be pre-bent to a particular configuration by an attending physician to facilitate insertion of the guidewire within the subject. First section 62 can be flattened by rolling or stamping to increase the flexibility of the guidewire's tip.

At the extreme distal tip portion of the guidewire, a weld 70, or other means of attachment such as brazing or soldering, attaches a radiopaque spring 80 to the corewire 36. The weld, solder or braze 70 defines a smooth hemispherical bead which does not damage the inner lining of the blood vessels as the guidewire tip comes in contact with those linings. The spring 80 is closely packed along the tapered core segment 62 so that adjacent coils 80a of the spring 80 are separated by a spacing or pitch distance of between 0.0005 and 0.002 inches with an optimum or preferred spacing of 0.001 inch. In one embodiment, the spring 80 is soldered or brazed (or bonded with epoxy) at connection 83 so that it is fixedly held by the corewire. In a second embodiment, a plastic sleeve engages a portion of the spring and overlies at least some of the coils of the spring to hold the spring on the corewire.

Figure 4:
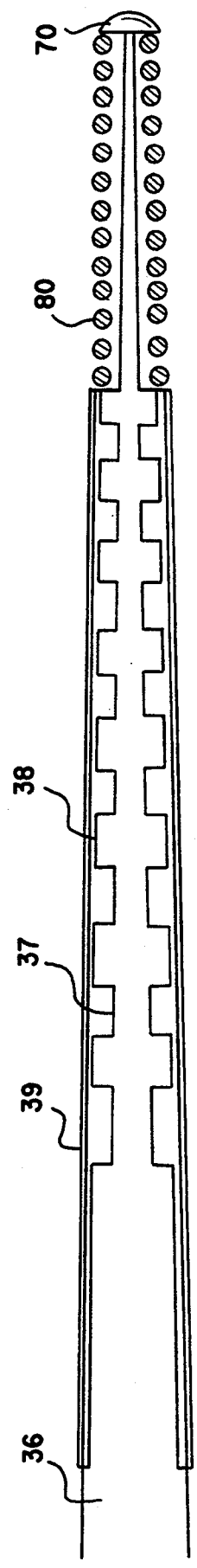
FIG. 4 is an elevational segmented view of the marker bands of one embodiment of the invention.

In second section 52, such as can be seen in FIG. 3, the grooves 37 and bands 38 can be formed to have the same length in the axial direction of the guidewire. As can also be seen in FIG. 3, the height of the bands can remain constant, or, the height of the bands can be variable, e.g., decreasing in a direction toward the weld 70. As can be seen in FIG. 4, the taper of bands 38 can be at a greater rate than the taper of an outer sleeve 39 such that the bands are increasingly disposed at a distance from sleeve 39 in the direction of weld 70. The width of the bands can likewise be made variable, such as increasing in length in the direction of weld 70. The length of the grooves can also be made variable if desired. Also, second section 52 can uniformly taper as in FIG. 3, and/or have non-tapering portions of uniform diameter. Bands 38 can be provided in a tapered portion of the guidewire as illustrated in FIGS. 3 and 4, or in a non-tapering portion having uniform diameter. The above considerations can depend on the desired application, the desired position and degree of radiopacity along the guidewire, and/or the flexibility requirements of the guidewire.

As can be further seen in FIG. 4, a polymer or polyimide thin wall sleeve 39 is provided to cover the banded second section of the guidewire. Outer sleeve 39 provides for a uniform flat external surface for the banded region of the guidewire. Grooves 37 covered by sleeve 39 can be filled with a non-radiopaque material such as a polymer or polyimide.

In order to form the guidewire of the present invention, the core is made, for example, by first forming an extruded rod or a drawn rod. For forming a drawn rod, the core material is drawn through successively smaller sizing dies. The taper of the core is formed, for example, by grinding down the core to achieve the desired degree of taper. The band/groove first section 52 can be formed by rotating the core and grinding at predetermined locations along the core so as to form the alternating bands and grooves having the desired dimensions.

The core is preferably metallic and provides radiopacity to the banded second section of the guidewire. The core material can be made from gold, platinum, titanium, tantalum, stainless steel, etc. (or alloys thereof, such as nitinol), though from a cost perspective, stainless steel is preferred. Alternatively, the core can be formed by mixing a polymer with a slurry providing radiopacity, e.g., a metallic slurry such as a titanium or tantalum slurry. Or, the core can be formed of a non-radiopaque material with the grooves filled with a metal or polymer/metallic slurry. And, whether formed from a metal or a polymer/metallic slurry, the core can be formed from a material different from, and less radiopaque than, spring 80 attached at the far distal end of the guidewire.

As with the corewire, spring 80 is formed from a radiopaque material, such as tantalum, titanium, platinum, gold, or alloys thereof. The spring is attached to the corewire by bonding with epoxy, welding, soldering or brazing. In the alternative, or in addition, to the above methods of attaching the spring, sleeve 39 can be positioned so as to overlie at least some of the coils of the spring so as to hold the spring on the corewire.

The polymer or polyimide sleeve can formed as a thin-walled sleeve having a constant thickness, or may fill in grooves 37 so as to have an increased sleeve thickness at places where the grooves are formed in the core. The sleeve can be made from one or more polymers or polyimides, such as polyethylene or polytetrafluoroethylene (PTFE). Sleeve 39 is not radiopaque and is disposed on the guidewire to cover the banded second section up to a point at which coils 80 are connected or adhered to the core 36. The sleeve is preferably heat bonded, swaged, melted, or otherwise attached at both its distal and proximal ends, to core 36.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. A guidewire comprising:
   a) an elongated corewire having a tapered first section at a far distal portion of the corewire, and a tapered second section proximal to said first section;
   b) a coiled radiopaque spring surrounding said first section of said corewire and attached to said corewire; and
   c) a plurality of grooves cut into said second section of said corewire with each pair of adjacent grooves defining therebetween a marker band unitary with the core wire.

2. The guidewire according to claim 1, further comprising a sleeve disposed around said corewire in said second section.

3. The guidewire according to claim 2, wherein said sleeve comprises at least one of a polymer and a polyimide.

4. The guidewire according to claim 3, wherein said sleeve comprises at least one of polyethylene and polytetrafluoroethylene.

5. The guidewire according to claim 1, wherein said coiled radiopaque spring is soldered, brazed or epoxy-bonded to said corewire.

6. The guidewire according to claim 2, wherein said sleeve is heat bonded, swaged or melted to said corewire.

7. The guidewire according to claim 1, wherein said corewire and integral radiopaque bands comprise at least one of gold, nitinol, platinum, titanium, tantalum and stainless steel.

8. The guidewire according to claim 1, wherein said corewire and integral radiopaque bands comprise a polymer with a metallic slurry.

9. The guidewire according to claim 8, wherein said metallic slurry is a titanium or tantalum slurry.

10. The guidewire according to claim 1, wherein said corewire is made of a less radiopaque material than said spring.

11. A method of making a guidewire comprising:
    a) extruding or drawing a rod to form a corewire of predetermined thickness;
    b) forming a taper in said corewire by grinding so as to achieve a desired degree of taper in adjacent first and second sections of said corewire; and
    c) forming alternating grooves and bands in the second section of said corewire which is proximal to said first section, by cutting a plurality of grooves at predetermined positions into said second section of said corewire with each pair of adjacent grooves defining therebetween a marker band unitary with the corewire.

12. The method according to claim 11, further comprising attaching a spring to said corewire so as to surround said first section of said corewire.

13. The method of claim 12, wherein said corewire and said spring are formed of radiopaque materials.

14. The method of claim 13, wherein said radiopaque materials comprise at least one of titanium, tantalum, nitinol, platinum, gold, and stainless steel.

15. The method of claim 11, wherein the corewire is formed by drawing through successively smaller sizing dies.

16. The method of claim 13, wherein said corewire is made of a less radiopaque material than said spring.

17. A method of making a guidewire comprising:
a) extruding or drawing a rod to form a corewire of predetermined thickness;
b) forming a taper in said corewire by grinding so as to achieve a desired degree of taper in adjacent first and second sections of said corewire; and
c) forming alternating grooves and bands in the second section of said corewire which is proximal to said first section, by grinding a plurality of grooves at predetermined position along said second section of said corewire such that said bands are formed integrally from said corewire;
the method further comprising attaching a spring to said corewire so as to surround said first section of said corewire, said corewire and said spring being formed of radiopaque materials; and
attaching a sleeve to said corewire so as to surround said unitary marker bands in said second section of said sleeve.

18. A method of making a guidewire comprising:
a) extruding or drawing a rod to form a corewire of predetermined thickness;
b) forming a taper in said corewire by grinding so as to achieve a desired degree of taper in adjacent first and second sections of said corewire; and
c) forming alternating grooves and bands in the second section of said corewire which is proximal to said first section, by grinding a plurality of grooves at predetermined position along said second section of said corewire such that said bands are formed integrally from said corewire;
the method further comprising attaching a spring to said corewire so as to surround said first section of said corewire, said corewire and said spring being formed of radiopaque materials which comprise at least one of titanium, tantalum, nitinol, platinum, gold, and stainless steel; and
wherein said unitary marker bands are formed to have a height progressively decreasing toward said first section of said corewire.

* * * * *